US009597659B2

(12) United States Patent
Bazer-Bachi et al.

(10) Patent No.: US 9,597,659 B2
(45) Date of Patent: Mar. 21, 2017

(54) HETEROGENEOUS CATALYST OF THE ZINC ALUMINATE SPINEL TYPE SURSTOICHIOMETRIC IN ZINC AND USE THEREOF IN A PROCESS FOR PREPARATION OF ALCOHOL ESTERS FROM TRIGLYCERIDES AND ALCOHOLS

(75) Inventors: Delphine Bazer-Bachi, Saint-Genis-Laval (FR); Vincent Coupard, Villeurbanne (FR); Sylvie Maury, Charly (FR); Veronique Pugnet, Lyons (FR); Isabelle Clemencon, Thurins (FR); Anne-Agathe Quoineaud, Lyons (FR)

(73) Assignee: IFB Energies nouvelles, Rueil-Malmaison (FR)

( * ) Notice: Subject to any disclaimer, the term of this patent is extended or adjusted under 35 U.S.C. 154(b) by 660 days.

(21) Appl. No.: 12/903,444

(22) Filed: Oct. 13, 2010

(65) Prior Publication Data

US 2011/0092730 A1 Apr. 21, 2011

(30) Foreign Application Priority Data

Oct. 14, 2009 (FR) ..................... 09 04932

(51) Int. Cl.
*C07C 69/00* (2006.01)
*B01J 21/02* (2006.01)
(Continued)

(52) U.S. Cl.
CPC ........... *B01J 23/005* (2013.01); *B01J 37/033* (2013.01); *C07C 67/03* (2013.01); *C11C 3/003* (2013.01); *Y02E 50/13* (2013.01)

(58) Field of Classification Search
CPC ........ B01J 23/005; B01J 37/03; B01J 37/033; C07C 67/03; C07C 69/24
(Continued)

(56) References Cited

U.S. PATENT DOCUMENTS 2,623,020 A * 12/1952 Gilbert ......................... 502/307
4,260,845 A * 4/1981 Shioyama ..................... 585/640
(Continued)

FOREIGN PATENT DOCUMENTS

| EP | 1460124 A1 | 9/2004 |
|---|---|---|
| EP | 1468734 A1 | 10/2004 |
| FR | 2794768 A1 | 12/2000 |

OTHER PUBLICATIONS

Institut National De La Propriete Industrielle. "Search Report." FR0904932, Applicant:IFP, Jun. 22, 2010.
(Continued)

*Primary Examiner* — Jun Li
(74) *Attorney, Agent, or Firm* — Millen, White, Zelano and Branigan, P.C.

(57) ABSTRACT

A catalyst with a mixed zinc and aluminum oxide base having a spinel structure surstoichiometric in zinc, in which part of the Zn atoms are in the octahedral position, a process for preparation of the same and use of the same in a process for preparation of a compound of linear monocarboxylic acid alcohol esters with 6-26 carbon atoms from a vegetable or animal oil, neutral or acid, virgin or recycled, with monoalcohols of 1-18 carbon atoms allowing an ester that can be used as a motor fuel or a heating fuel and a pure glycerine to be obtained directly in one or more steps.

15 Claims, 1 Drawing Sheet

(51) Int. Cl.
  *B01J 37/03* (2006.01)
  *B01J 37/06* (2006.01)
  *B01J 37/08* (2006.01)
  *B01J 23/00* (2006.01)
  *C07C 67/03* (2006.01)
  *C11C 3/00* (2006.01)

(58) Field of Classification Search
  USPC .......................... 502/103, 113, 342; 560/129
  IPC ............................................ B01J 23/005,23/06
  See application file for complete search history.

(56) References Cited

U.S. PATENT DOCUMENTS

| | | | |
|---|---|---|---|
| 5,908,946 A * | 6/1999 | Stern et al. | 554/167 |
| 6,297,180 B1 * | 10/2001 | Maier | 501/12 |
| 2003/0195380 A1 * | 10/2003 | Demmering et al. | 568/885 |
| 2004/0234448 A1 | 11/2004 | Hillion et al. | |
| 2005/0113588 A1 * | 5/2005 | Hillion et al. | 554/174 |

OTHER PUBLICATIONS

Pugnet, V. et al. "Stability, activity and selectivity study of a zinc aluminate heterogeneous catalyst for the transesterification of vegetable oil in a batch reactor." (Applied Catalysis A: General), pp. 71-78, vol. 374, No. 1-2, Feb. 1, 2010.

Rossi, P. F. et al. "Surface Basicity of Mixed Oxides: Magnesium and Zinc Aluminates." (Langmuir, American Chemical Society), pp. 2677-2681, vol. 7, No. 11, Nov. 1, 1991.

Thevenot, F. et al. "Preparation and Characterization of Al-Rich Zn-Al Hydroalcite-like Compounds." (Clays and Clay Minerals) pp. 396-402, vol. 37, No. 5, Jan. 1, 1989.

Espacenet Database. "English abstract—Process for the manufacture of fatty acid esters from ricin oil and mono-alcohols uses a heterogeneous catalyst based on zinc and aluminum with a spinel structure in a transesterification reaction and separation." FR2794768A1, Applicant: IFP, Dec. 15, 2000.

* cited by examiner

HETEROGENEOUS CATALYST OF THE ZINC ALUMINATE SPINEL TYPE SURSTOICHIOMETRIC IN ZINC AND USE THEREOF IN A PROCESS FOR PREPARATION OF ALCOHOL ESTERS FROM TRIGLYCERIDES AND ALCOHOLS

AREA OF THE INVENTION

The present invention relates to the area of catalysts used in transesterification processes with a view to obtaining esters of fatty substances that can be used as diesel fuels. More specifically, the invention relates to a heterogeneous catalyst of the zinc aluminate spinel type surstoichiometric in zinc and use thereof in a process for preparation of monocarboxylic acid alcohol esters from fatty substances of vegetable or animal origin.

The principal intended reaction is a transesterification carried out in accordance with flow diagram I below and possibly coupled with reactions performed according to flow diagram II below.

Flow Diagram I:

1 triglyceride+3 alcohols⇌3 fatty substance esters+1 glycerine

Flow Diagram II:

1 fatty acid+1 alcohol⇌1 fatty acid esters+1 water 1 fatty acid+1 glycerine⇌1 fatty acid glyceride+1 water

PRIOR ART

Fatty substance esters are currently used in numerous applications as diesel fuels, domestic fuels, ecologically sound solvents, base compounds for the production of fatty alcohol sulphonates, amides, ester dimers, and so on.

In the case of diesel fuel, which is nowadays a major application of fatty substance esters, a certain number of specifications have been prepared which are listed, along with the limits and methods, in standard EN 14214 (2003) which is currently applicable in Europe. The ester must contain at least 96.5% by weight of esters, a maximum of 0.8% by weight of monoglycerides, a maximum of 0.2% by weight of diglycerides and a maximum of 0.2% by weight of triglycerides, a low level of free fatty acids (<0.5 mg of KOH per g), that may be corrosive, less than 0.25% by weight of free and bonded glycerine and only trace metals. A precise method is therefore involved in obtaining the desired purity.

When an ester is produced from an oil or fat and mono-alcohol, depending on the type of oil employed at the outset, a co-product, glycerine, automatically forms at 10%-15% by weight. This glycerine can be put to good use in various applications, but has to be purified first (removal of metals, salts and water). In order to achieve this purity vacuum bidistillation is often necessary.

In summary, the majority of commercial processes for the production of esters easily arrive at raw products (esters and glycerine), but these have to be thoroughly purified by various treatments that ultimately put up the price of the conversion.

It is known to produce methyl esters by conventional methods of homogeneous catalysis with soluble catalysts such as soda or sodium methylate, by reacting a neutral oil with an alcohol such as methanol (for example JAOCS 61, 343-348 (1984)). However, a pure product that can be used as a motor fuel and glycerine conforming to the standards are only arrived at after a large number of steps. In fact, the glycerine obtained is polluted by the alkaline salts or the alcoholates, such that the glycerine purification plant is almost as expensive as that by which the ester is produced.

Heterogeneous catalysis processes offer the advantage of producing esters and glycerine that are catalyst-free and therefore easy to purify. However, it is often difficult to simultaneously obtain an ester and a highly pure glycerine in an economical fashion.

Numerous metal oxides have been used to catalyse the transesterification reaction. This was the case recently with zinc oxide doped with lithium (Xie et al., *Ind. Eng. Chem. Res.*, 2007, 10.1021/ie070597s) or barium (Xie et al, *Catalysis Letters* (2007) 117, 159-165). Reddy et al. (*Energy Fuels*, 2006, 20, 1310) propose the use of nanocrystalline calcium oxide which, due to the formation, in the presence of methanol, of species of $Ca(OMe)_2$, has the behaviour of an essentially heterogeneous catalyst. A number of authors have also studied the behaviour of magnesium oxide (Dossin et al., *Applied Catalysis B*, 2006, 61, 33-45). These alkaline earth metal oxides have non-zero solubilities in methanol (Gryglewicz, *Bioresour. Technol.*, 1999, 70, 249), which poses problems of leaching and stability of the catalysts causing a major drop in activity at the recycling stage and pollution of the effluents from the reaction, resulting in a need to purify these to meet the required specifications. The solution proposed for the zinc oxide-based catalysts, consisting of regenerating the catalyst by impregnation of lithium or barium nitrate, cannot be adapted for industrial use. Moreover, the leached metallic species are found in the ester and glycerine products, causing a deterioration in their quality and non-conformity with the specifications applicable to diesel. European patent EP-B-0 198 243 describes the production of methyl esters by transesterification of an oil with methanol, using as a catalyst an alumina or a mixture of an alumina and ferrous oxide. However, the liquid hourly space velocity (volume of oil injected/volume of catalyst/hour) is low, the quantity of glycerine gathered is much lower than the theoretical forecast and the purity of the esters obtained is fairly low (93.5-98%).

Processes using a catalytic system based on metal oxides alone or in association, by deposition or not on alumina, have been described. Patent FR-B-2 752 242, in the name of the present applicant, describes the use of solid and non-soluble catalysts formed for zinc and aluminium precursors. The solid used in this patent is of the general formula $ZnAl_2O_4$, x ZnO, y $Al_2O_3$, where x and y are between 0 and 2. This solid can be prepared by co-precipitation at a pH of 6-8.

Generally speaking, the solids obtained by co-precipitation can be of different types depending on the operating conditions selected (ratio between the zinc and aluminium precursors, calcination temperature, pH, conditions under which reagents are added, etc.). Where a Zn/Al molar ratio of 0.5 is used a direct spinel type solid may be obtained of formula $ZnAl_2O_4$ (gahnite). For higher Zn/Al ratios, it is possible to obtain solids surstoichiometric in zinc. Rossi, P. F. et al Surface basicity of Mixed oxides: Magnesium and Zinc Aluminates. Langmuir 7, 2677-2681 (1991) describe a mixture of ZnO and zinc aluminates, with said mixture having a Zn/Al atomic ratio of above 0.5. These solids have a high basicity in terms of strength but not in terms of numbers. The increased basic strength of these solids can be attributed to the ZnO present in the solid. These solids are not used as catalysts in transesterification reactions.

Generally speaking, the structure of the direct spinels (or true spinels) consists of a compact cubic arrangement in lattices with centred faces of oxygen. The bivalent cations ($Zn^{2+}$) occupy the tetrahedral coordination sites and the trivalent cations ($Al^{3+}$) the octahedral coordination sites. In the case of an inverse spinel structure, the tetrahedral coordination sites are occupied by trivalent cations and the octahedral coordination sites are occupied by di- and trivalent cations.

Surprisingly, the inventors have discovered that the method of synthesis by co-precipitation of aluminium and zinc precursors and application of certain operating conditions, specifically a constant pH of 6.1-6.9, preferably 6.3-6.9 during synthesis and a Zn/Al atomic ratio of 0.53-0.60, preferably of 0.56-0.58, allows a single spinel phase surstoichiometric in zinc to be obtained and in which part of the zinc atoms occupy octahedral sites. This surstoichiometry in zinc gives the material a catalytic action that is of interest in transesterification reactions of fatty substances and allows yields of esters to be obtained that are much higher than those achieved with a stoichiometric solid (Zn/Al=0.5). The fact that this zinc aluminate-based solid is in particular free of ZnO allows the problems of Zn leaching in the ester and glycerine products, causing a deterioration in them and their non-conformity to the specifications required by standard EN 14214 applicable to biodiesel, to be avoided.

DETAILED DESCRIPTION OF THE INVENTION

The present invention relates to a heterogeneous catalyst with a zinc aluminate base of the spinel type surstoichiometric in zinc, its process for preparation and its and use thereof in a process for preparation of monocarboxylic acid alcohol esters from fatty substances of vegetable or animal origin.

The catalyst has a zinc aluminate base, free from ZnO, alumina or $ZnAl_2O_4$, the zinc aluminate phase of which consists of a single zinc aluminate of the spinel type surstoichiometric in zinc in which the Zn/Al atomic ratio is 0.53-0.60, preferably 0.56-0.58. At least part of the zinc is in the octahedral position of the spinel structure.

Said catalyst is prepared by co-precipitation of precursors of aluminium and zinc in a Zn/Al atomic ratio of 0.53-0.60, preferably of 0.56-0.58.

Said spinel structure catalyst is surstoichiometric in zinc in relation to $ZnAl_2O_4$, but without containing ZnO or alumina phases; the excess of zinc, in relation to the stoichiometry being situated in an octahedral position rather than the tetrahedral position as in the case of true spinels.

Although not containing ZnO, these solids have other specific basic properties (large number of basic sites) consistent with their improved catalytic activity compared with a stoichiometric $ZnAl_2O_4$ phase. For a Zn/Al ratio of 0.63, a ZnO phase is detected by XRD and in this case the strength of the basic sites increases.

The catalyst used in the present invention is preferably prepared according to a process comprising:
- a co-precipitation step involving the mixing of precursors of zinc II and aluminium III in the presence of a base, at a pH of 6.1-6.9, preferably 6.3-6.9, and at a temperature of 30-50° C.;
- a filtration step of the precipitate obtained;
- an optional washing step to remove the residual species;
- a drying step at a temperature of 80-175° C., preferably for a period of 12-24 hours;
- a calcination step in the presence of oxygen at a temperature of 500-800° C., preferably for a steady period of 1-4 hours.

The precursors can be selected from among the salts of zinc and aluminium: nitrate, sulphate, acetate, chloride, for example, from among the alkoxides of zinc and aluminium. Aluminium, may also be introduced in the form of sodium aluminate. The precipitation may be performed using an aqueous solution of sodium carbonate or of sodium hydrogen carbonate, alone or in conjunction with a solution of ammonia or soda or any other base allowing the pH to be maintained during the synthesis. The synthesis may also be performed using a base alone: soda, ammonia, or any other base allowing the pH to be controlled or also a solution of sodium aluminate. The pH may be adjusted by an acid in the event of basic precursors being used.

The zinc surstoichiometry in zinc associated with this mode of synthesis by co-precipitation allows a single spinal phase to be obtained with zinc atoms in the octahedral position and gives the material an interesting catalytic action.

The mixed oxide obtained is characterised by X-ray diffraction (XRD), NMR, IR and $CO_2$ microcalometry.

Characterisation of the Structure by XRD:

The structure of these materials is characterised by X-ray diffraction on powder with the aim of determining the lattice parameter and the stoichiometry of the spinel.

The most intense positions of the experimental rays observed for these solids are as follows: $31.2°2\theta$, $36.8°2\theta$, $44.7°2\theta$, $49°2\theta$, $55.6°2\theta$, $59.3°2\theta$, $65.1°2\theta$, $74°2\theta$, $77.2°2\theta$, $90.8°2\theta$ and $93.9°2\theta$. These correspond to the rays of a spinel.

The lattice parameter and the stoichiometry of the solid can be determined by refining the X-ray diffraction diagrams using the Rietveld method which is a conventional method known to a person skilled in the art.

This method consists of minimising the integrated differences in intensity between an experimental diagram and the diagram calculated using crystallographic models of the phases present, by refinement of the ray profiles and the structural parameters, in particular the levels of occupation of the tetrahedral and octahedral sites of the lacunar spinel type structure. Two types of constraints were imposed in order to obtain reasonable solutions: maintenance of the elementary composition of the mixture and electroneutrality.

The level of occupation by Zn and Al of the octahedral and tetrahedral sites of the true spinel phase varies.

The level of occupation is the ratio between the number of atoms per site and the number of equivalents of the general position (192 for the spinel structure). It represents the electronic density of each site (28 e- for $ZN^{2+}$ and 10 e- for $AL^{3+}$).

If the balance of the positive charges [$Zn^{2+}$ (tetra)+$Al^{3+}$ (octa)] is not equal to the balance of the negative charges provided by the $O^{2-}$ ions, then equilibrium between the charges is re-established either by a contribution of $Al^{3+}$ ions in the tetrahedral position if there is a deficit of positive charges, or by a contribution of $Zn^{2+}$ ions in the octahedral position in the opposite case. The constraints applied to the system are maintenance of the electronic density measured on each site and electroneutrality of the lattice. The results of the characterisation by XRD allow the stoichiometric composition to be arrived at that exhibits surstoichiometry in zinc. The increase in the content of zinc causes an increase in the lattice parameter.

Characterisation of the Structure by NMR:

The structure of the solid may also undergo Nuclear Magnetic Resonance (NMR) characterisation. The aluminium atoms present in the zinc aluminate catalysts are present in a tetrahedral ($Al^{IV}$) and octahedral ($Al^{VI}$) geometry. From a quantitative point of view, the proportions of the various aluminium species can be determined by decomposition of the $^{27}$Al MQMAS and MAS spectra in order to correct the intensity of their dependence at the quadripolar interaction. The NMR of the $^{27}$Al performed with the help of magic angle spinning (MAS) and multiquanta MAS (MQMAS) techniques shows a change in the local geometry and in the electronic state of the aluminic sites. For catalysts substoichiometric in zinc, the zinc takes up the tetrahedral position, and the relative quantity of tetrahedral aluminium falls. The spinel formed is a direct spinel. For the catalysts surstoichiometric in zinc that are the subject matter of this invention, the zinc takes up the octahedral position involving a change to the quadripolar parameters of the octahedral aluminiums and a reduction in their relative proportion. These results are perfectly in keeping with the analysis by X-ray diffraction.

These solids surstoichiometric in zinc have specific basic properties consistent with their improved catalytic action in relation to a stoichiometric $ZnAl_2O_4$ phase. The number and strength of the basic sites can be characterised by techniques well known to a person skilled in the art such as infrared spectroscopy with probe molecules or microcalorimetry.

Characterisation of the Basic Acid Balance (Number of Sites) by Absorption of Probe Molecules and IR Spectroscopy:

Acetonitrile is an amphoteric probe molecule of low basicity used to characterise both the basicity and the acidity. It gives access to a base/acid balance of the surface studied. Thanks to its electron doublet on the nitrogen atom, the molecule behaves as a base or electron donor. The adsorption at ambient temperature of $CH_3CN$ is expressed as a disturbance of the vibration frequencies of the hydroxyl groups and of the CN bond. The adsorption of $CH_3CN$ also allows characterisation of a number of basic sites. Its adsorption at these sites leads to the formation of $CH_2CN$ anion:

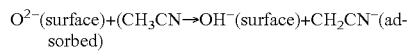
$O^{2-}$(surface)+($CH_3CN\rightarrow OH^-$(surface)+$CH_2CN^-$(adsorbed)

The adsorption brings into play the acid/base character of the $O^-/OH^-$ and $CH_3CN/CH_2CN^-$ pairings and a cationic site for stabilising the $CH_2CN^-$ anion. The wavelength $v(C\equiv N)$ of the carbonisation characterises the cationic centre. So for the ZnO the wavelength $v(C\equiv N)$ is 2121 cm$^{-1}$.

This technique for characterisation of the type spinel solids surstoichiometric in zinc shows that the number of basic sites is much higher in spinel type solids surstoichiometric in zinc compared with the number of sites of stoichiometric gahnite.

Characterisation of the Strength of Basic Sites by $CO_2$ Microcalorimetry:

In order to measure the change in strength of the basic sites as a function of the Zn content of the solids, measurements of heat of adsorption of $CO_2$ by microcalorimetry were performed on these materials. They show that the strength of the sites remains roughly the same for the solids that are the subject matter of the invention.

The texture (specific surface area) of the mixed oxide is characterised by nitrogen volumetric analysis. The material used in the present invention also has an atomic ratio Zn/Al of 0.53-0.60 and a specific surface area of 45-155 m$^2$/g.

Transesterification

The present invention also describes a process for preparation of a compound of linear monocarboxylic acid alcohol esters with 6-26 carbon atoms and glycerine in which a fatty substance of animal or vegetable origin is reacted with an aliphatic monoalcohol containing 1-18 carbon atoms, in the presence of at least one zinc aluminate based catalyst free from ZnO, alumina or $ZnAl_2O_4$, the zinc aluminate phase of which consists of a single spinel type zinc aluminate phase surstoichiometric in zinc in which the atomic ratio Zn/Al is 0.53-0.60, preferably 0.56-0.58.

The spinel containing zinc atoms in the octahedral position gives the material a catalytic action that is of interest.

Fatty Substances

The fatty substances used in the process of the invention correspond to natural or processed substances, of animal or vegetable origin, containing a majority of triglycerides, commonly termed oil and fats.

The oils that can be used include all standard oils such as palm (concrete or oleine), soya, palm kernel, copra, babassu, rapeseed (old or new), sunflower (conventional or oleic), corn or cottonseed oils, peanut, curcas (*Jatropha curcas*), castor, flaxseed and crambe oils and all oils resulting for example from sunflower or rapeseed genetic modification or hybridation or also originating from algae.

Frying, rendering and various animal oils may also be used, such as fish, seal and rendering oils, tallow, lard or also fats resulting from the treatment of waste water and also poultry fat, as the esters manufactured from certain alcohols such as ethyl, isopropyl or butyl alcohol allow the pour point to be reduced by more than 10° C. and thus the use of more saturated oils from the outset.

The oils used also include oils that have been partially modified by, for example, polymerisation or oligomerisation, such as for example the stand oils of flaxseed and sunflower oils and blown vegetable oils.

The oils used are neutral or acid, virgin or recycled.

The presence of fatty acid in the oils is not on the face of it detrimental. However, in the case of oils with a very strong acidity index (close to 10 mg of KOH/g), one possibility is to precede the transesterification reaction by an esterification reaction of the free fatty acids present, either by using the same alcohol as used in the transesterification process in the presence of a strong acid such as sulphuric acid or soluble or supported sulphonic acids (of the Amberlyst 1500 resin type), or preferably using glycerine with the same catalytic system as employed for the transesterification reaction, in order to form a total or partial glycerol ester, at atmospheric pressure and preferably in a vacuum and at temperatures of 150-220° C.

When frying oils are used, which represent a very cheap raw material for producing biodiesel, it is necessary to remove the fatty acid polymers from the reaction mixture in order for the mixture of esters to meet the specifications of standard EN 14214.

Alcohol

The type of the alcohol employed in the process plays a role in the transesterification activity.

Generally speaking, it is possible to use various aliphatic monoalcohols containing, for example, 1-18 carbon atoms, preferably 1-12 carbon atoms.

In a more preferred manner, the aliphatic monoalcohol contains 15 carbon atoms.

The most active is methyl alcohol. However, ethyl alcohol and isopropyl, propyl, butyl, isobutyl and even amyl alcohols can be envisaged. Heavier alcohols such as ethyl-hexyl alcohol or lauric alcohol may also be used.

Advantageously methyl alcohol may also be added to the heavy alcohols to facilitate the reaction.

Moreover, when the ethyl ester is prepared, a mixture of ethyl and methyl alcohol can be used containing 1-50% by weight, preferably 1-10% by weight, of methyl alcohol in order to increase the conversion.

Transesterification Reaction Operating Conditions

The process is carried out at temperatures of 130° C.-220° C., at internal pressures of less than 10 MPa with an excess of monoalcohol in relation to the stoichiometric fatty substance/alcohol. Following the reaction the excess alcohol is evaporated off and the glycerine separated, preferably by decantation.

Generally, the reaction can be carried out according to various modes of operations.

If a discontinuous reaction is employed, one or two steps can be used, that is to say performing an initial reaction of up to 85%-95% conversion to esters, cooling with evaporation of the excess alcohol, decanting the glycerine and completion of the reaction by reheating to 130° C.-220° C. and adding alcohol in order to obtain a complete conversion. A 98% conversion to esters can also be aimed for by working for a sufficiently long period in a single step under appropriate conditions, for example by increasing the temperature and/or the alcohol/fatty substance ratio.

If a continuous reaction is undertaken, a number of autoclaves and decanters can be used. In the first case, a partial conversion is performed most often of less than 90% and generally approximately 85%, then the alcohol is decanted with evaporation and cooling; in a second reactor the transesterification reaction is completed under the conditions stated with the addition of part of the alcohol evaporated previously. Finally the excess alcohol is evaporated in an evaporator and the glycerine and the esters are separated by decantation.

If a fixed bed continuous process is selected, it is advantageous to work at temperatures of 130-220° C., preferably 150-180° C., and at pressures of 1-7 MPa, with a liquid hourly space velocity preferably of 0.1-3, preferably 0.3-2, in the first step and with a weight ratio of alcohol/oil varying from 3/1 to 0.1/1.

Thus at the end of these two steps, a biodiesel is obtained that meets the specifications. The level of conversion is adjusted in order to obtain a motor fuel ester that meets the specification and a high purity glycerine using one or two steps.

The ester and the glycerine obtained do not contain impurities from the catalyst. As a result, no purification treatment will be applied in order to eliminate the catalyst or the residues of this unlike catalysts working according to a homogenous process for which the catalyst or its residues are, following the reaction, located in the same phase as the ester and/or the glycerine.

The action and selectivity of this catalyst is not affected by the transesterification or esterification reaction: the catalyst is stable and recyclable under the experimental conditions of the reaction. This type of catalyst is compatible with use in a continuous industrial process, for example in a fixed bed, and in which the charge of the catalyst can be used for a very long period without loss of action. The catalyst used in the present invention may be implemented in the form of powders, pellets, extrudates or balls.

The resistance to leaching of the catalyst is verified by a measurement of the content of dissolved trace metals from the catalyst both in the ester formed and in the glycerine produced, of less than 1 ppm, and by the stability of the action of the catalyst over time.

EXAMPLES

The following examples illustrate the invention without limiting its scope, with Example 1 being provided by way of comparison.

Example 1 relates to the preparation of a solid by blending, wherein the ratio of Zn/Al is in the range covered by the invention but wherein the crystalline phases differ from the solid according to the invention. It contains in particular a ZnO phase.

Example 2 illustrates in a non-restrictive manner, the preparation of a series of catalysts according to the invention, prepared by co-precipitation and the characterisation of these.

Example 3 presents the catalytic tests and illustrates the catalytic interest of the solids according to the invention.

The X ray diffraction measurements are carried out using a Bragg-Brentano type powder diffractometer in $\theta$-$\theta$ configuration and fitted mainly with copper X-ray tube ($\lambda$=1.5402 Å), a rear monochromator and a point detector. The recording conditions are as follows: tube power of 35 kV by 35 mA, sampling pitch 0.04°2$\theta$, counting time in 10 s steps. The angular area explored goes from 2 to 100°2$\theta$.

The sample were analysed by NMR MAS and MQMAS of the aluminium 27 with the help of a Bruker Avance 400 MHz (9.4 T) spectrometer in 4 mm probe. The pulse sequences used are MAS selective (low radiofrequency field of the order of 30 kHz and pulse angle $\pi$/12) and MQMAS "z-filter" synchronised on the rotation speed, respectively. The speed of rotation is 14 kHz.

The solids are characterised by IR in transmission mode with the help of a ThermoFischer spectrometer of the Nexus type, fitted with a DTGS or MCT detector.

The spectra are obtained following Fourier transformation of 69 interferogrammes accumulated between 4,000 and 90 $cm^{-1}$ with a resolution of 4 $cm^{-1}$.

The characterisation of the acido-basicity is performed via the adsorption of the acetornitrile (probe molecule). This is performed by the addition of controlled quantities with the help of a standard volume and a pressure measurement gauge. Prior to the adsorption a sample activation step is performed. This is a thermal treatment under secondary vacuum (10 hours at 500° C. under $10^{-6}$ Torr).

Preparation of the sample before IR characterisation is performed in the following way: 20 mg of solid are compressed at 150 kg/$cm^2$ in the form of a self-supporting pellet of 16 mm in diameter.

The basicity of the solids was also studied through the adsorption of $CO_2$ by microcalorimetry. The apparatus used was a SETARAM TG-DSC-111 instrument. The samples are first activated at 500° C. under a helium flow and then brought back to 100° C. A flow of $CO_2$ is then brought into contact with the sample at 100±0.01° C. and the variation in weight of the sample and the thermal events are measured simultaneously.

Example 1 (Comparative)

Preparation of a Reference Solid A1 by Blending

The solid A1 is prepared by blending a boehmite and zinc oxide in the presence of 5.8% nitric acid in solution in water, in order to obtain a composition of the material whose elementary analysis is 37% Zn and 28.6% Al (Zn/Al=0.54).

The catalyst is extruded with a 3 mm diameter die and undergoes thermal treatment at 650° C. for 2 hours.

The surface area of the solid A1 is 149 $m^2$ $g^{-1}$.

The X-ray diffraction allows a quantitative determination of the various phases. Zinc oxide ZnO and two solids solutions, one rich in zinc and the other rich in aluminium, are detected.

The analysis by structural refinement allows the composition of each of these phases to be arrived at $Zn_{0.7}Al_2O_{3.7}$ (51%, lattice parameter 8.08 Å) and $Zn_{0.33}Al_2O_{3.33}$ (22%, lattice parameter 8.01 Å).

Example 2

Preparation of Solids B1, B2, B3, B4 and B5

The solid is obtained by combined precipitation of the precursors of zinc and aluminium (aqueous solution of zinc nitrate and aluminium nitrate), such that the Zn/Al ratio is equal to the ratio aimed for in the final material (here 0.28, 0.50, 0.56, 0.58 and 0.63), respectively, for the materials with notation B1, B2, B3, B4 and B5 at a constant pH of 6.5. The pH is kept constant through the addition of a base (ammonia in aqueous solution 225 g/l) throughout the synthesis.

The synthesis takes place as follows:

A water blanket is introduced into a double walled borosilicate glass reactor fitted with baffles and then heated to 40° C. while being agitated by a mobile device with three inclined blades.

The precursors and the base are introduced into the reactor via a pumping system allowing regulation of the introduction deliveries and the duration of the synthesis. Control of the pH is provided by the base pump delivery: this is kept constant at 6.5±0.2 throughout the co-precipitation.

Then the contents of the reactor are filtered on the Büchner. The cake obtained is dried at 150° C. for 16 hours in a ventilated oven and then calcined at 650° C. (ramp of 5° C./minute and level stage of 2 hours at 650° C.) in a muffle furnace.

An analysis by X-ray fluorescence (XRF) was carried out on the five materials. The contents obtained following correction for loss due to burning carried out at 550° C., 4 hours, resulted in the Zn/Al ratios presented in Table 1.

The X-ray diffraction allows a determination of their lattice parameter. All these data are shown in Table 1.

TABLE 1

Principal structural and elementary characteristics of the solids

| Preparation method Notation | Atomic ratio Zn/Al (FX) | Lattice parameter following refinement (Å) | % ZnO |
|---|---|---|---|
| Co-blended A1 (non-conforming) | 0.54 | 8.08 8.01 | 27.5 |
| Co-precipitated B1 (non-conforming) | 0.28 | 8.066 | 0 |
| Co-precipitated B2 (non-conforming) | 0.50 | 8.089 | 0 |
| Co-precipitated B3 (conforming) | 0.56 | 8.095 | 0 |
| Co-precipitated B4 (conforming) | 0.58 | 8.097 | 0 |
| Co-precipitated B5 (non-conforming) | 0.63 | 8.096 | 5 |

The solid A1 is prepared by blending and contains ZnO. The solid B1 is a spinet type zinc aluminate substoichiometric in zinc (not conforming to the invention). The solid B32 is stoichiometric (not conforming to the invention). The solids B3 and B4 are spinet type zinc aluminates surstoichiometric in zinc according to the invention. The solid B5 is a spinet type zinc aluminate surstoichiometric in zinc with an atomic ratio of 0.63 (not conforming to the invention). In the case of B5 the appearance of a ZnO phase is noticed.

The increase in the zinc content causes an increase in the lattice parameter. For a Zn/Al ratio of 0.56, the lattice parameter of the solid exceeds that of the stoichiometric spinet $ZnAl_2O_4$ (8.09 Å).

The specific surface area of the five solids B1 to B5 was estimated by volumetric analysis with nitrogen at low temperature in accordance with standards ASTM D 3663-84 or NFX 11-621: it was 155 m²/g, 74 m²/g, 76 m²/g, 58 m²/g and 46 m²/g, respectively, for solids B1, B2, B3, B4 and 85.

The surface sites present (strength/number) on these solids were characterised by quantification of the acid/base balance by IR with acetonitrile adsorption and by microcalorimetry.

BRIEF DESCRIPTION OF THE DRAWINGS

The IR with acetonitrile probe molecule shows a jump in the number of basic sites when moving from the direct spinel to the spinels in which part of the zinc atoms are located in the octahedral position.

Figure 1:
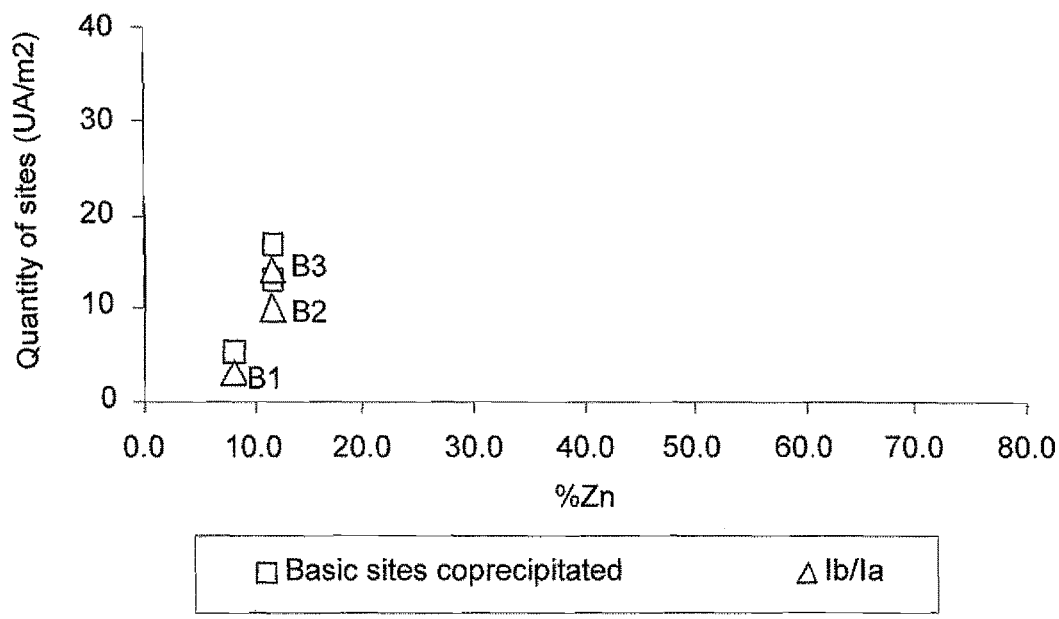
FIG. 1 shows the effect of the zinc content on the number of basic sites and the base/acid balance measured by acetonitrile as a function of the zinc content. The number of basic sites increased greatly (from 12 to 17 UA/m²) when changing from a ZN/Al of 0.5 (B2) to 0.56 (B3).
Figure 2:
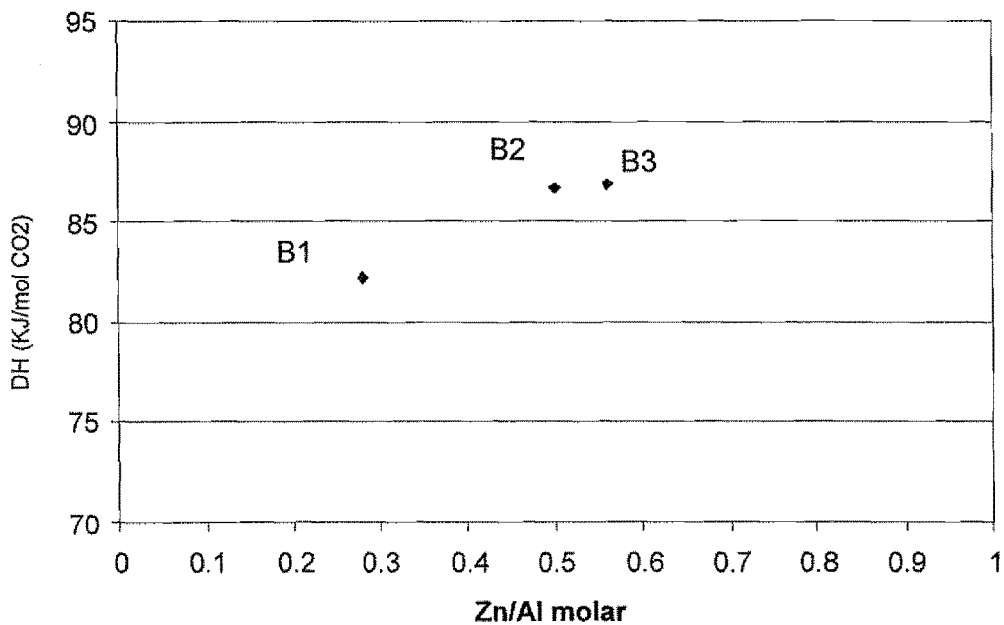
FIG. 2 shows the effect of the zinc content on the heat of adsorption of the $CO_2$ on the solids, measured by microcalorimetry. It will be noted that the strength of the basic sites is equivalent for solids B2 and B3.

Finally, an increase can be seen in the number of basic sites without an increase in their strength coupled with the insertion, in the single spinel type phase constituting the solid, of zinc atoms in the octahedral position, the latter phenomenon taking place when the Zn/Al ratio is above 0.5 (corresponding to the stoichiometry of the true spinel).

Example 3

Testing of the Catalysts: Comparative Catalytic Activities of the Different Solids of Variable Zn/Al, B1, B2, B3, B4 and B5

Solids A1 and B1 to B5 were tested as catalysts in a transesterification reaction of a fatty substance.

These tests were carried out in a batch reactor and therefore in a single step. In order to obtain a biodiesel meeting the specifications, it would be necessary to proceed at the end of this first step with a decantation following evaporation of the alcohol and cooling of the medium, then separation of the glycerine and of the ester phase, then to complete the transesterification reaction by adding back to the ester fraction part of the evaporated alcohol.

The oil used in these examples is food grade rapeseed oil, the fatty acid composition of which is as follows:

TABLE 2

Composition of the rapeseed oil

| Fatty acid glyceride | Type of fatty chain | % by weight |
|---|---|---|
| Palmitic | C16:0 | 5 |
| Palmitoleic | C16:1 | <0.5 |
| Stearic | C18:0 | 2 |
| Oleic | C18:1 | 59 |
| Linoleic | C18:2 | 21 |
| Linolenic | C18:3 | 9 |
| Arachidic | C20:0 | <0.5 |
| Gadoleic | C20:1 | 1 |
| Behenic | C22:0 | <0.5 |
| Erucic | C22:1 | <1 |

However, any other oil of vegetable or animal origin could provide similar results.

Analyses of Products by Quantitative Analysis of Glycerides and Esters of the Ester Phase Samples are taken in a regular manner during the test in order to follow the progress of the reaction. The samples taken are washed in an aqueous solution saturated with NaCl then, following decantation, the higher organic phase, diluted in THF, analysed by GPC (Gel Permeation Chromatography—or steric exclusion chromatography). The steric exclusion chromatography allows separation of the products according to the steric size/dimension.

The equipment used is a WATER. HPLC device, fitted with 3 Waters styragel columns (THF) with a molar mass scale of 0-1,000 g·mol-1. These columns are placed in a thermostatically-controlled oven at 40° C. The detector is a Waters 2414 refractometer.

Catalytic Test:

Into a closed reactor at ambient temperature 25 g of rapeseed oil, 25 g of methanol and 1 g of catalyst prepared as described in Example 1 or Example 2 in powder form are introduced. The weight ratio of methanol to oil is thus 1, corresponding to a molar ratio of 27.5. The reactor is then closed, stirred (200 rpm) and heated to 200° C. using a heating magnetic stirrer. The temperature of the reaction medium is stabilised at 200° C. after 30 minutes of heating. The pressure is the autogeneous pressure of the alcohol at the working temperature, that is approximately 40 bar. Monitoring of the reaction starts when the temperature of the reaction medium has reached the setpoint, with the samples being taken after 1, 2 and 4 hours, and the samples being analysed as described by GPC. The following table summarises the results obtained for the samplings after 1, 2 and 4 hours of reaction for A1 and B1 to B5.

TABLE 3

% RME (rapeseed methyl ester) in the glyceride phase over time for the tests carried out with the series of solids A1, B1, B2, B3, B4 and B5.

| | Sampling time (h) | | |
|---|---|---|---|
| | 1 | 2 | 4 |
| A1 (non-conforming) | 11.8 | 25.6 | 55.4 |
| B1 (non-conforming) | 9.9 | 16.3 | 28.1 |
| B2 (non-conforming) | 13.8 | 29.3 | 58.7 |
| B3 (conforming) | 26.3 | 58.6 | 85.4 |
| B4 (conforming) | 55.3 | 79.2 | 86.0 |
| B5 (non-conforming) | 74.5 | 81.4 | 86.2 |

For conversions that are remote from the thermodynamic equilibrium (1 and 2 h reaction), the yield of RME with solid B3 is twice as high as the yield obtained with solid B2. Solids B3 and B4 allow ester yields to be obtained that are vastly higher than those obtained with the stoichiometric solid B2. B5 demonstrates a very high activity linked to the appearance of a ZnO phase. Its catalytic activity is in part linked to these zinc species leached into the reaction medium, and moreover the strength of these basic sites of ZnO is greater than that of the direct spinels. The fact that solids B3 and B4 are notably free of ZnO allows the problems of Zn leaching to be avoided in the ester and glycerine products while achieving a catalytic activity comparable with that of the catalyst containing ZnO.

Without further elaboration, it is believed that one skilled in the art can, using the preceding description, utilize the present invention to its fullest extent. The preceding preferred specific embodiments are, therefore, to be construed as merely illustrative, and not limitative of the remainder of the disclosure in any way whatsoever.

The entire disclosures of all applications, patents and publications; cited herein and of corresponding FR application Ser. No. 09/04.932, filed Oct. 14, 2009, are incorporated by, reference herein.

From the foregoing description, one skilled in the art can easily ascertain the essential characteristics of this invention and, without departing from the spirit and scope thereof, can make various changes and modifications of the invention to adapt it to various usages and conditions.

The invention claimed is:

1. A catalyst with a zinc aluminate base, free from ZnO, alumina and $ZnAl_2O_4$, the zinc aluminate base of which comprises a single zinc aluminate phase of the spinel type surstoichiometric in zinc in which a portion of the zinc atoms occupy octahedral sites and the Zn/Al atomic ratio is 0.56-0.58, said catalyst prepared by a process comprising:
   a) co-precipitation involving the mixing of precursors of zinc II and aluminium III in a Zn/Al atomic ratio of 0.56-0.58, in the presence of a base, at a pH of 6.1-6.9, and at a temperature of 30-50° C.;
   b) filtration of precipitate obtained;
   c) optionally washing to remove residual species;
   d) drying at a temperature of 80-175° C.;
   e) calcination in the presence of oxygen at a temperature of 500-800° C.

2. A process for preparation of the catalyst according to claim 1, comprising the following steps:
   a) a co-precipitation step involving the mixing of precursors of zinc II and aluminium III in a Zn/Al atomic ratio of 0.56-0.58, in the presence of a base, at a pH of 6.1-6.9, and at a temperature of 30-50° C.;
   b) a filtration step of the precipitate obtained;
   c) an optional washing step to remove the residual species;
   d) a drying step at a temperature of 80-175° C.;
   e) a calcination step in the presence of oxygen at a temperature of 500-800° C.

3. A preparation process according to claim 2, in which said precursors of zinc II and aluminium III are chosen from nitrate, sulphate, acetate and chloride salts of zinc and/or aluminium, zinc and/or aluminium alkoxides and sodium aluminate.

4. A preparation process according to claim 2 in which said base is chosen from an aqueous solution of sodium carbonate, an aqueous solution of sodium hydrogen carbonate, a solution of ammonia, a solution of soda, a solution of sodium aluminate or mixtures of at least two of these solutions.

5. A process according to claim 2 conducted at a pH of 6.3-6.9.

6. A preparation process according to claim 3 in which said base is an aqueous solution of sodium carbonate, an aqueous solution of sodium hydrogen carbonate, a solution of ammonia, a solution of soda, a solution of sodium aluminate or mixtures of at least two of these solutions.

7. A process for the production of a compound of linear monocarboxylic acid alcohol esters with 6-26 carbon atoms and glycerine, in which comprising reacting a fatty substance of vegetable or animal origin with an aliphatic alcohol containing 1-18 carbon atoms, in the presence of at least a catalyst according to claim 1.

8. A process according to claim 7, wherein the aliphatic alcohol is methanol.

9. A process according to claim 7, conducted at a temperature of 130° C.-220° C., and an internal pressure of less than 10 MPa and in an excess of aliphatic alcohol in relation to the stoichiometric fatty substance/alcohol.

10. A process according to claim 7, comprising evaporating the aliphatic alcohol and separating the glycerine.

11. A process according to claim 7 comprising performing the reaction discontinuously.

12. A process according to claim 7 comprising performing the reaction continuously, on a fixed bed or with autoclaves and decanters in series.

13. A process according to claim 12, comprising performing the reaction on a fixed bed, at a temperature of 130-220° C., at a pressure of 1-7 MPa, and a liquid hourly space velocity of 0.1-3, with an alcohol/fatty substance weight ratio of 3/1-0.1/1.

14. A process according to claim 7 wherein the fatty substance is palm (concrete or oleine), soya, palm kernel, copra, babassu, rapeseed (old or new), sunflower (conventional or oleic), corn, cotton seed oils, peanut, jatropha, castor, flaxseed oil, crambe oil, algae, sunflower or rapeseed oils obtained by genetic modification or hybridation, an oil partially modified by polymerisation or oligomerisation, a frying or rendering oil, a fish or seal oil, poultry fat, tallow, lard, or fat resulting from treatment of waste waters.

15. A process according to claim 7, wherein the catalyst is in powder, extrudate, ball or pellet form.

* * * * *